(12) United States Patent
Van Dyke et al.

(10) Patent No.: US 10,716,603 B2
(45) Date of Patent: Jul. 21, 2020

(54) IMPLANTS FOR BRIDGING OSSEOUS DEFECTS

(71) Applicant: Biomet Manufacturing, LLC, Warsaw, IN (US)

(72) Inventors: William Scott Van Dyke, Warsaw, IN (US); Frank A Liporace, Englewood Cliffs, NJ (US); Dan Dziadosz, Tampa, FL (US); Jordan Grossman, Warsaw, IN (US); Jordi Asuncion Marquez, Warsaw, IN (US); Paul Thomas Slagle, Leesburg, IN (US); George J Haidukewych, Orlando, FL (US); David Thordarson, Warsaw, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 0 days.

(21) Appl. No.: 15/901,221

(22) Filed: Feb. 21, 2018

(65) Prior Publication Data

US 2018/0235678 A1 Aug. 23, 2018

Related U.S. Application Data

(60) Provisional application No. 62/461,387, filed on Feb. 21, 2017.

(51) Int. Cl.
*A61B 17/72* (2006.01)
*A61F 2/28* (2006.01)
(Continued)

(52) U.S. Cl.
CPC .............. *A61B 17/72* (2013.01); *A61F 2/28* (2013.01); *A61F 2/4202* (2013.01);
(Continued)

(58) Field of Classification Search
CPC .............. A61F 2/28; A61F 2002/30354; A61F 2002/30224; A61B 17/72; A61B 17/7283; A61B 17/68; A61B 17/7216
See application file for complete search history.

(56) References Cited

U.S. PATENT DOCUMENTS 4,938,768 A 7/1990 Wu
5,935,127 A 8/1999 Border
(Continued)

FOREIGN PATENT DOCUMENTS

| CN | 102813564 | 12/2015 |
|---|---|---|
| CN | 110678150 A | 1/2020 |
| WO | 2018156563 | 8/2018 |

OTHER PUBLICATIONS

"International Application Serial No. PCT US2018 018927, International Search Report dated May 8, 2018", 7 pgs.
(Continued)

*Primary Examiner* — Brian A Dukert
(74) *Attorney, Agent, or Firm* — Schwegman Lundberg & Woessner, P.A.

(57) ABSTRACT

Various modular implants and modular implant systems are disclosed herein, as are methods of implanting the same. The modular implant systems can include modular implants that are stacked on each other to define a modular implant system, which in an example can be used to replace or augment a void in bone. The modular implants can interact with an intramedullary implant to, for instance, assist with a fusion procedure.

20 Claims, 10 Drawing Sheets

(51) Int. Cl.
  *A61F 2/42*  (2006.01)
  *A61F 2/30*  (2006.01)
(52) U.S. Cl.
  CPC .......... *A61F 2002/3093* (2013.01); *A61F 2002/30224* (2013.01); *A61F 2002/30354* (2013.01); *A61F 2002/30507* (2013.01); *A61F 2002/30622* (2013.01); *A61F 2002/4205* (2013.01); *A61F 2310/00011* (2013.01)

(56) References Cited

U.S. PATENT DOCUMENTS

| | | |
|---|---|---|
| 6,120,504 A | 9/2000 | Brumback et al. |
| 6,264,699 B1 | 7/2001 | Noiles et al. |
| 6,319,286 B1 | 11/2001 | Fernandez et al. |
| 6,454,810 B1 | 9/2002 | Lob |
| 6,569,203 B1 | 5/2003 | Keller |
| 6,613,092 B1 | 9/2003 | Kana et al. |
| 6,723,129 B2 | 4/2004 | Dwyer et al. |
| 6,843,808 B2 | 1/2005 | Grundei |
| 6,869,450 B2 | 3/2005 | Grundei |
| 6,953,479 B2 | 10/2005 | Carson et al. |
| 6,981,991 B2 | 1/2006 | Ferree |
| 7,018,420 B2 | 3/2006 | Grundei |
| 7,192,448 B2 | 3/2007 | Ferree |
| 7,323,012 B1 | 1/2008 | Stone et al. |
| 7,435,263 B2 | 10/2008 | Barnett et al. |
| 7,507,256 B2 | 3/2009 | Heck et al. |
| 7,691,150 B2 | 4/2010 | Cronin et al. |
| 7,794,503 B2 | 9/2010 | Daniels et al. |
| 7,909,883 B2 | 3/2011 | Sidebotham |
| 7,993,408 B2 | 8/2011 | Meridew et al. |
| 8,021,432 B2 | 9/2011 | Meridew et al. |
| 8,157,869 B2 | 4/2012 | Metzger et al. |
| 8,292,967 B2 | 10/2012 | Brown et al. |
| 8,444,699 B2 | 5/2013 | Metzger et al. |
| 8,496,711 B2 * | 7/2013 | Anapliotis ............ A61F 2/3836 623/16.11 |
| 8,535,386 B2 | 9/2013 | Servidio et al. |
| 8,932,364 B2 | 1/2015 | Mooradian et al. |
| 8,998,996 B2 | 4/2015 | James et al. |
| 9,452,056 B2 | 9/2016 | Early et al. |
| 2002/0040244 A1 | 4/2002 | Alfred, III et al. |
| 2003/0191531 A1 | 10/2003 | Berry et al. |
| 2004/0049270 A1 | 3/2004 | Gewirtz |
| 2004/0193267 A1 | 9/2004 | Jones et al. |
| 2005/0004679 A1 | 1/2005 | Sederholm et al. |
| 2005/0071014 A1 | 3/2005 | Barnett et al. |
| 2005/0107794 A1 | 5/2005 | Hazebrouck |
| 2006/0036251 A1 | 2/2006 | Reiley |
| 2006/0036322 A1 | 2/2006 | Reiley |
| 2006/0229730 A1 | 10/2006 | Railey et al. |
| 2007/0129809 A1 | 6/2007 | Meridew et al. |
| 2007/0156241 A1 | 7/2007 | Reiley et al. |
| 2008/0021566 A1 | 1/2008 | Peters et al. |
| 2008/0065212 A1 | 3/2008 | Zucherman |
| 2008/0154316 A1 | 6/2008 | Reiley |
| 2008/0281430 A1 | 11/2008 | Kelman et al. |
| 2008/0306603 A1 | 12/2008 | Reich et al. |
| 2009/0011384 A1 | 1/2009 | Collins et al. |
| 2009/0216334 A1 | 8/2009 | Leibel |
| 2009/0259261 A1 | 10/2009 | Reiley |
| 2010/0003640 A1 | 1/2010 | Damstra et al. |
| 2010/0094292 A1 | 4/2010 | Parrott |
| 2010/0179658 A1 | 7/2010 | Freeman et al. |
| 2010/0292738 A1 | 11/2010 | Reiley |
| 2010/0298947 A1 | 11/2010 | Unger |
| 2011/0087294 A1 | 4/2011 | Reiley |
| 2011/0087296 A1 | 4/2011 | Reiley et al. |
| 2011/0118796 A1 | 5/2011 | Reiley et al. |
| 2011/0178604 A1 | 7/2011 | Porter |
| 2011/0202141 A1 | 8/2011 | Metzger et al. |
| 2011/0208189 A1 | 8/2011 | Faccioli et al. |
| 2011/0208315 A1 | 8/2011 | Anapliotis et al. |
| 2012/0197255 A1 | 8/2012 | Elghazly |
| 2013/0204384 A1 | 8/2013 | Hensley et al. |
| 2013/0204387 A1 | 8/2013 | Meridew et al. |
| 2014/0025181 A1 | 1/2014 | Vanasse et al. |
| 2014/0099601 A1 | 4/2014 | Bassett et al. |
| 2014/0277532 A1 | 9/2014 | Teeny et al. |
| 2014/0277538 A1 | 9/2014 | Sander |
| 2015/0134071 A1 | 5/2015 | Luna et al. |
| 2015/0173904 A1 | 6/2015 | Stark |
| 2016/0089138 A1 | 3/2016 | Early et al. |
| 2016/0089245 A1 * | 3/2016 | Early .................. A61F 2/4202 623/21.18 |
| 2016/0338842 A1 | 11/2016 | Adams |

OTHER PUBLICATIONS

"International Application Serial No. PCT US2018 018927, Written Opinion dated May 8, 2018", 7 pgs.
"U.S. Appl. No. 14/499,537, Response filed Jan. 25, 2016 to Restriction Requirement dated Nov. 23, 2015", 6 pgs.
"U.S. Appl. No. 14/499,537, Non Final Office Action dated Feb. 24, 2016", 11 pgs.
"U.S. Appl. No. 14/499,537, Notice of Allowance dated Jul. 27, 2016", 7 pgs.
"U.S. Appl. No. 14/499,537, Response filed May 24, 2016 to Non Final Office Action dated Feb. 24, 2016", 6 pgs.
"U.S. Appl. No. 14/499,537, Restriction Requirement dated Nov. 23, 2015", 7 pgs.
Horisberger, et al., "Commercially Available Trabecular Metal Ankle Interpositional Spacer for Tibiotalocalcaneal Arthrodesis Secondary to Severe Bone Loss of the Ankle", The Journal of Foot & Ankle Surgery 53, (2014), 383-387.
"Chinese Application Serial No. 201880013069.4, Notification to Make Rectification dated Sep. 6, 2019", (W/ English Translation), 2 pgs.
"Australian Application Serial No. 2018225123, First Examination Report dated Sep. 27, 2019", 3 pgs.
"Australian Application No. 2018225123, Response filed Dec. 17, 2019 to First Examination Report dated Sep. 27, 2019", 26 pgs.

* cited by examiner

IMPLANTS FOR BRIDGING OSSEOUS DEFECTS

PRIORITY APPLICATIONS

This application claims the benefit of priority to U.S. Provisional Application Ser. No. 62/461,387, filed Feb. 21, 2017, the content of which is hereby incorporated by reference in its entirety.

FIELD OF THE DISCLOSURE

The present disclosure relates to surgical implant systems, including implants, instruments, and methods for installing an implant. Specifically, the present disclosure relates to intramedullary devices, instruments, and bone augments used therewith.

BACKGROUND

Intramedullary implants are used in various contexts, including to repair fractures or to achieve joint fusion (i.e., arthrodesis). In the case of arthrodesis, it is frequently necessary to apply compression across one (1) or more joints to bring the adjoining bones of the joint into apposition, and then fix the adjoining bones so that fusion can occur across the joint site. An intramedullary implant can be used to achieve fixation of the adjoining bones of the joint after compression and secure the bones in position to allow fusion to occur.

In some cases, bone augments can also be used with intramedullary implants to replace and/or augment a particular bone. This can be the case in instances where, for example, bone is diseased and/or some trauma has occurred to the bone and the bone needs to be replaced or augmented. U.S. Pat. No. 9,308,031 ("the '031 patent") discloses various intramedullary devices that are used for ankle fusion, as an example. The '031 patent is hereby incorporated by reference herein and is referred to below, in some instances. When bone augments are used with intramedullary implants, it is desirable to ensure that the bone augment cooperates with the intramedullary device and also that proper bone growth and/or fusion occurs when using the augment.

The present disclosure provides intramedullary implants, instruments, and methods that work in cooperation with bone augments to allow surgeons to conduct surgical repairs in a more effective manner, as described in more detail below.

SUMMARY

To better illustrate the system disclosed herein, a non-limiting list of examples is provided here:

Example 1 includes a modular implant system comprising a first modular implant part having first and second opposing surfaces and an inner core section, and a second modular implant part having first and second opposing surfaces and an inner core section, wherein the first and second modular implant parts are engageable and, when engaged, the inner core sections of the first and second modular implant parts collectively define an inner core of the modular implant system that has a shape that corresponds to a shape of a portion of an intramedullary implant.

In Example 2, the system of Example 1 can optionally further comprise a third modular implant part having first and second opposing surfaces and an inner core section, and a fourth modular implant part having first and second opposing surfaces and an inner core section, wherein the third and fourth modular implant parts are engageable and, when engaged, the inner core sections of the third and fourth modular implant parts collectively define an inner core of the modular implant system that has a shape that corresponds to the shape of the portion of the intramedullary implant, and wherein the second surfaces of the third and fourth modular implant parts are engageable with the second surfaces of the first and second modular implant parts, such that the third and fourth implant parts are arrangeable on the first and second modular implant parts in a stacked configuration.

In Example 3, the first and second implant parts of the system of Example 2 can optionally have a first height and the third and fourth implant parts can have a second height that is different than the first height.

In Example 4, the system of any one of or any combination of Examples 2-3 can optionally include the second surface of the first modular implant part having a post and the first surface of the third modular implant part including a recess sized and shaped to receive the post.

In Example 5, the system of any one of or any combination of Examples 1-4 can optionally include the shape of the inner core of the modular implant system being round.

In Example 6, the system of any one of or any combination of Examples 1-4 can optionally include the first surface of any of the first and second modular implant parts being at least partially composed of a porous biocompatible material that has an architecture that replicates natural cancellous bone.

In Example 7, the system of claim 6 can optionally include the first surface of any of the first and second modular implant parts being at least partially composed of a substantially non-porous biocompatible material.

In Example 8, the system of any one of or any combination of Examples 1-7 can optionally include the inner core of the modular implant system being composed of a substantially non-porous biocompatible material.

In Example 9, the system of any one of or any combination of Examples 1-7 can optionally include the first modular implant part including a first locking hole and the second modular implant part including a first hole, and wherein when the first and second modular implant parts are engaged, the first locking hole and the first hole are aligned.

In Example 10, the system of claim 9 can optionally further comprise a fixation member insertable through the first hole and into the first locking hole, the fixation member being configured to engage the first locking hole and lockingly join the first modular implant part to the second modular implant part.

In Example 11, the system of any one of or any combination of Examples 2-4 or 5-10, when dependent from Example 2, can optionally include the first modular implant part having a second hole and the third modular implant part having a first locking hole, and wherein when the first modular implant part is stacked on the third modular implant part, the second hole and the first locking hole of the third modular implant part are aligned.

In Example 12, the system of Example 11 can optionally further comprise a fixation member insertable through the second hole and into the first locking hole of the third modular implant part, the fixation member being configured to engage the first locking hole of the third modular implant part and lockingly join the first modular implant part to the third modular implant part.

In Example 13, the system of any one of or any combination of Examples 9-12 can optionally include the first locking hole of the first modular implant part and the first locking hole of the third modular implant part being threaded.

Example 14 includes a method of implanting a modular implant system comprising implanting an intramedullary implant having a shaft into the medullary canal of a bone of a patient, positioning a first inner core section of a first modular implant part around a first portion of the shaft so that the first inner core section substantially conforms to the first portion of the shaft, positioning a second inner core section of a second modular implant part around a second portion of the shaft so that the second inner core section substantially conforms to the second portion of the shaft, and joining the first modular implant part with the second modular implant part so that the first and second inner core sections collectively define an inner core that substantially conforms to at least part of the shaft of the intramedullary implant.

In Example 15, the method of Example 14 can optionally include wherein the positioning steps occur after the intramedullary implant is implanted into the medullary canal of the bone.

In Example 16, the method of any one of or any combination of Examples 14-15 can optionally further comprise positioning a third inner core section of a third modular implant part around a third portion of the shaft so that the third inner core section substantially conforms to the third portion of the shaft, positioning a fourth inner core section of a fourth modular implant part around a fourth portion of the shaft so that the fourth inner core section substantially conforms to the fourth portion of the shaft, and joining the third and fourth modular implant parts with the first and second modular implant parts, wherein the first and second modular implant parts have a first height and the third and fourth modular implant parts have a second height that is greater than the first height.

In Example 17, the method of Example 16 can optionally further comprise joining the third modular implant part with the fourth modular implant part so that the third and fourth inner core sections collectively define an inner core that substantially conforms to at least part of the shaft of the intramedullary implant.

In Example 18, the method of any one of or any combination of Examples 14-17 can optionally further comprise locking the first modular implant part to the second modular implant part.

In Example 19, the method of any one of or any combination of Examples 16-17 can optionally further comprise locking the third and fourth modular implant parts to the first and second modular implant parts.

In Example 20, the method of any one of or any combination of Examples 16-17 and 19 can optionally further comprise stacking the first and second modular implant parts on the third and fourth modular implant parts.

BRIEF DESCRIPTION OF THE FIGURES

The above-mentioned and other features and advantages of this disclosure, and the manner of attaining them, will become more apparent and the disclosure itself will be better understood by reference to the following description of examples taken in conjunction with the accompanying drawings, wherein.

Corresponding reference characters indicate corresponding parts throughout the several views. The exemplifications set out herein illustrate examples of the disclosure, and such exemplifications are not to be construed as limiting the scope of the disclosure in any manner.

DETAILED DESCRIPTION

In describing the examples of the invention(s) illustrated and to be described with respect to the drawings, specific terminology will be used for the sake of clarity. However, the invention(s) is not intended to be limited to any specific terms used herein, and it is to be understood that each specific term includes all technical equivalents.

As used herein, the following directional definitions apply. Anterior and posterior mean nearer the front or nearer the rear of the body, respectively, proximal and distal mean nearer to or further from the root of a structure, respectively, and medial and lateral mean nearer the sagittal plane or further from the sagittal plane, respectively. The sagittal plane is an imaginary vertical plane through the middle of the body or a body structure that divides the body or body structure into right and left halves. In addition, the terms implant and prosthesis, and variations thereof, can be used interchangeably.

The present disclosure is directed at intramedullary implants, modular implant systems, and modular bone augments usable therewith. As detailed below, various modular implant systems can be comprised of a plurality of modular bone augments, which can be in multiple parts, to form a bone augment that can be used to replace and/or augment a patient's bone. As an example, the modular implant systems and bone augments described herein can be used to replace and/or augment a patient's talus bone in the ankle or part of the tibia (e.g., in instances where such bone is diseased or damaged).

Figure 1:
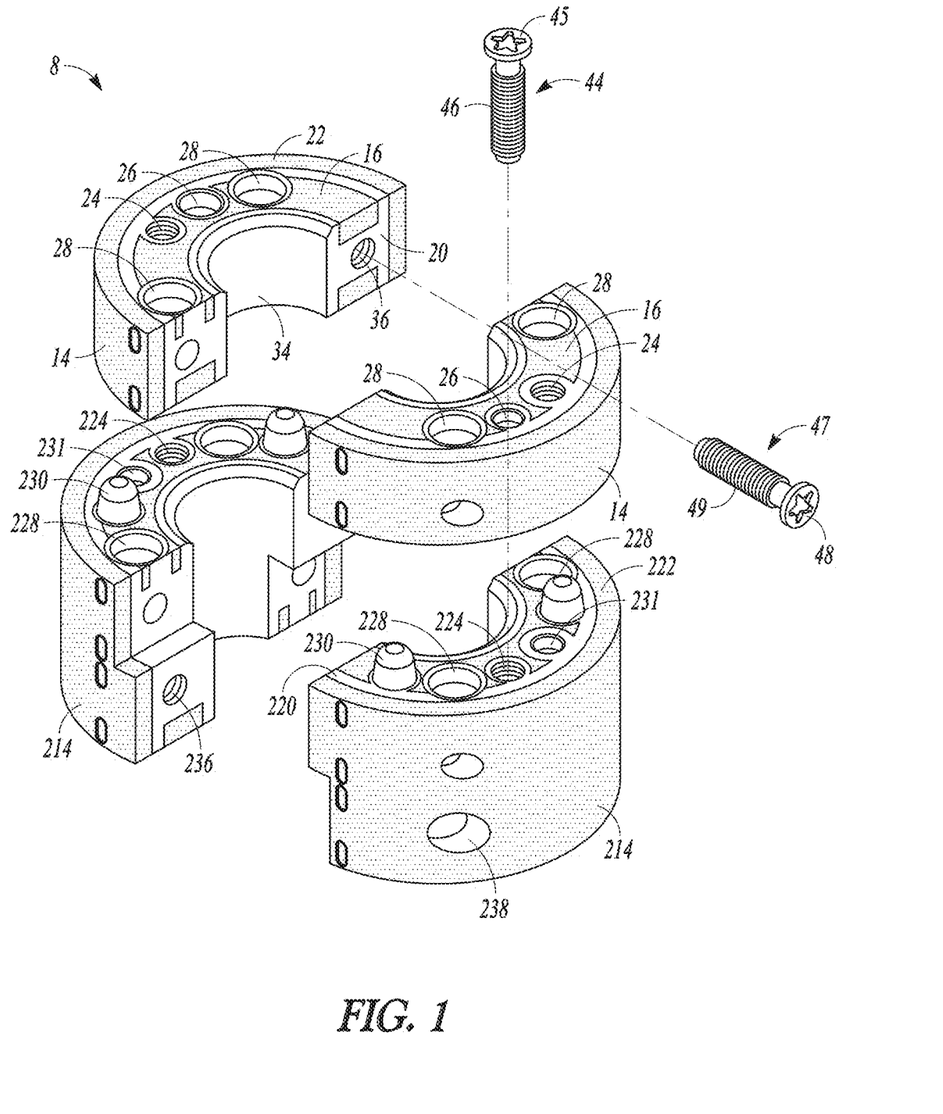
FIG. 1 is an exploded view of a modular implant system.

Referring to FIG. 1, an example of a modular implant system 8 is shown. Modular implant system 8 can include a series of modular implant parts 14, 214 that, collectively, can engage together to define modular implant system 8. For example, modular implant parts 14, 214 can be joined horizontally and can be stacked to any suitable vertical height to replace and/or augment bone during a surgical procedure.

An example of a modular implant part 14 is shown in FIGS. 1 and 3A-C. When arranged as a pair as shown in FIG. 1, first and second modular implant parts 14 can be mirror images of each other. In general, a pair or alternatively more than two (2) modular implant parts 14 can be joined together to form an augment.

Figure 3A:
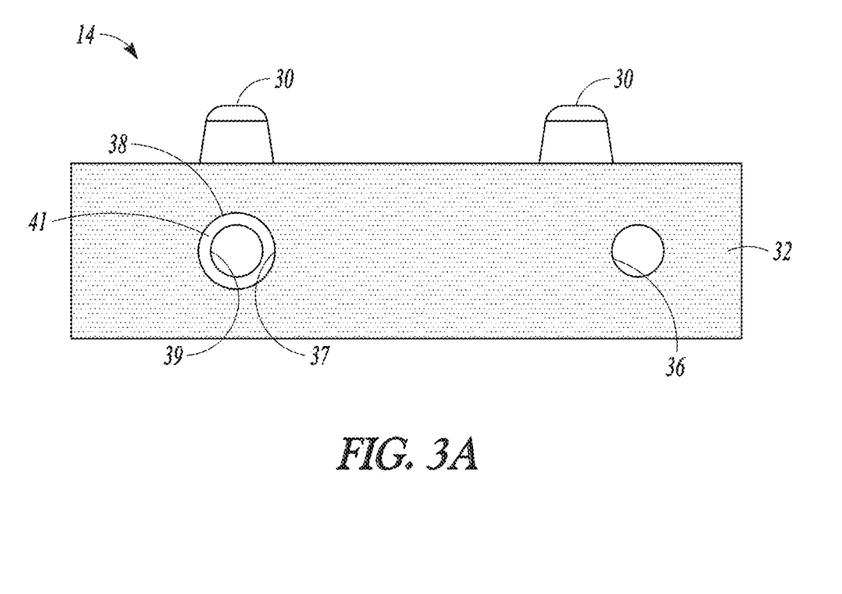
FIG. 3A is a side view of a first example of a modular implant part.
Figure 3B:
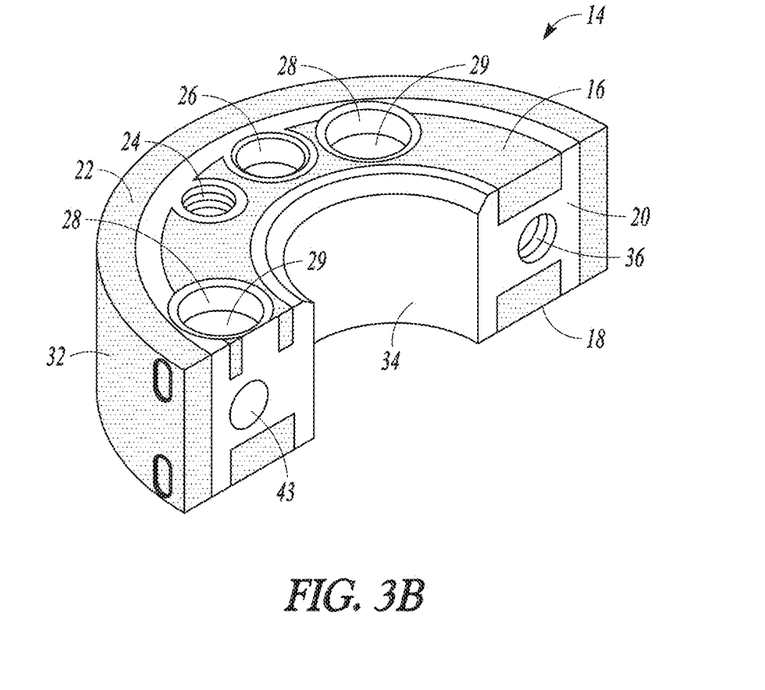
FIG. 3B is a bottom perspective view of the modular implant part of FIG. 3A.
Figure 3C:
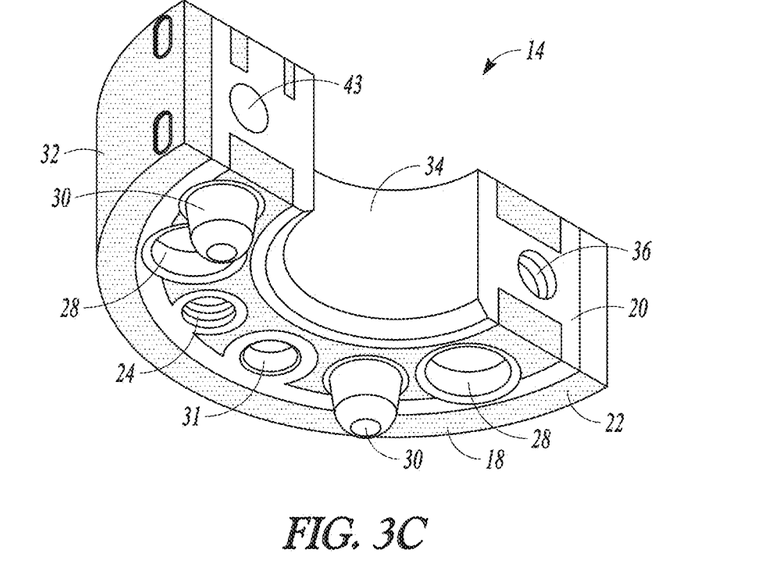
FIG. 3C is a top perspective view.
Figure 4A:
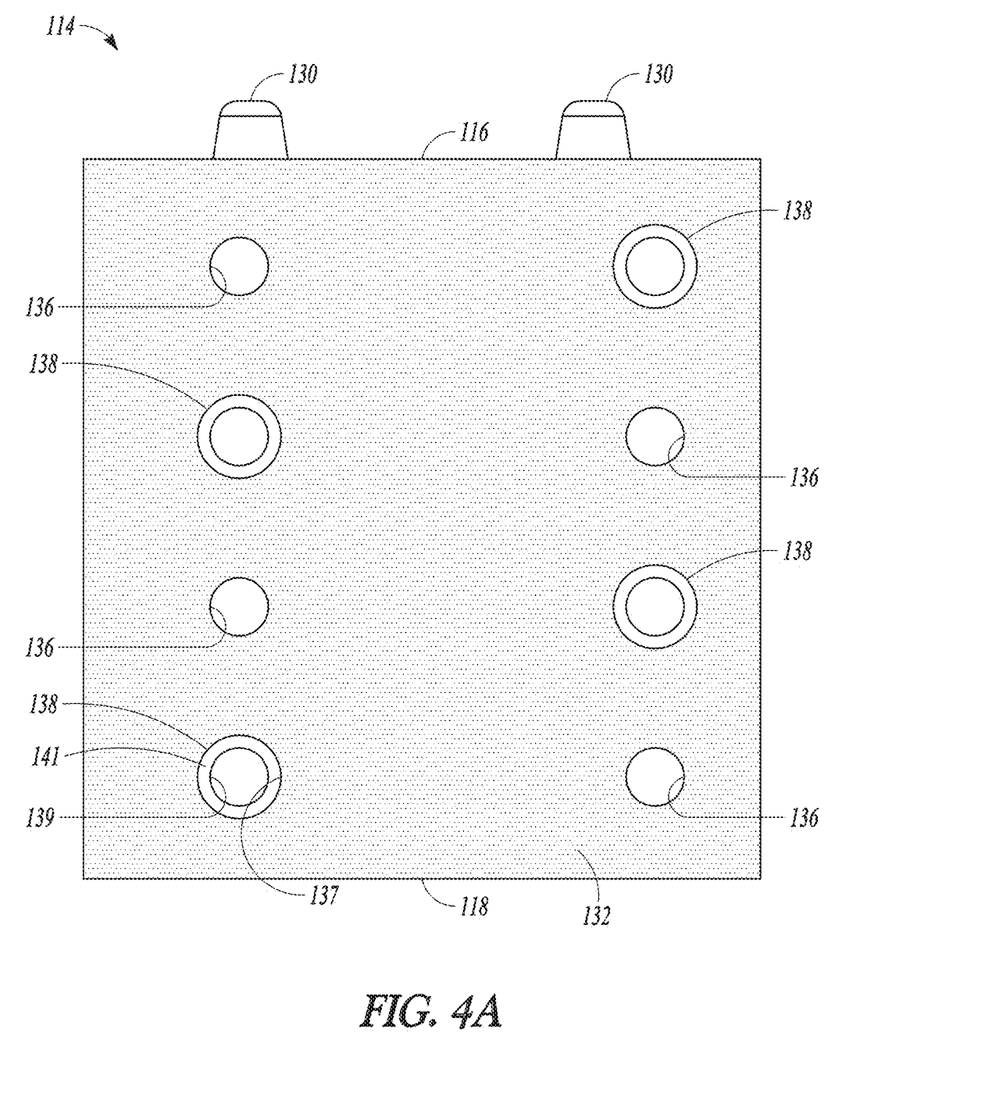
FIG. 4A is a side view of a second example of a modular implant part.
Figure 4B:
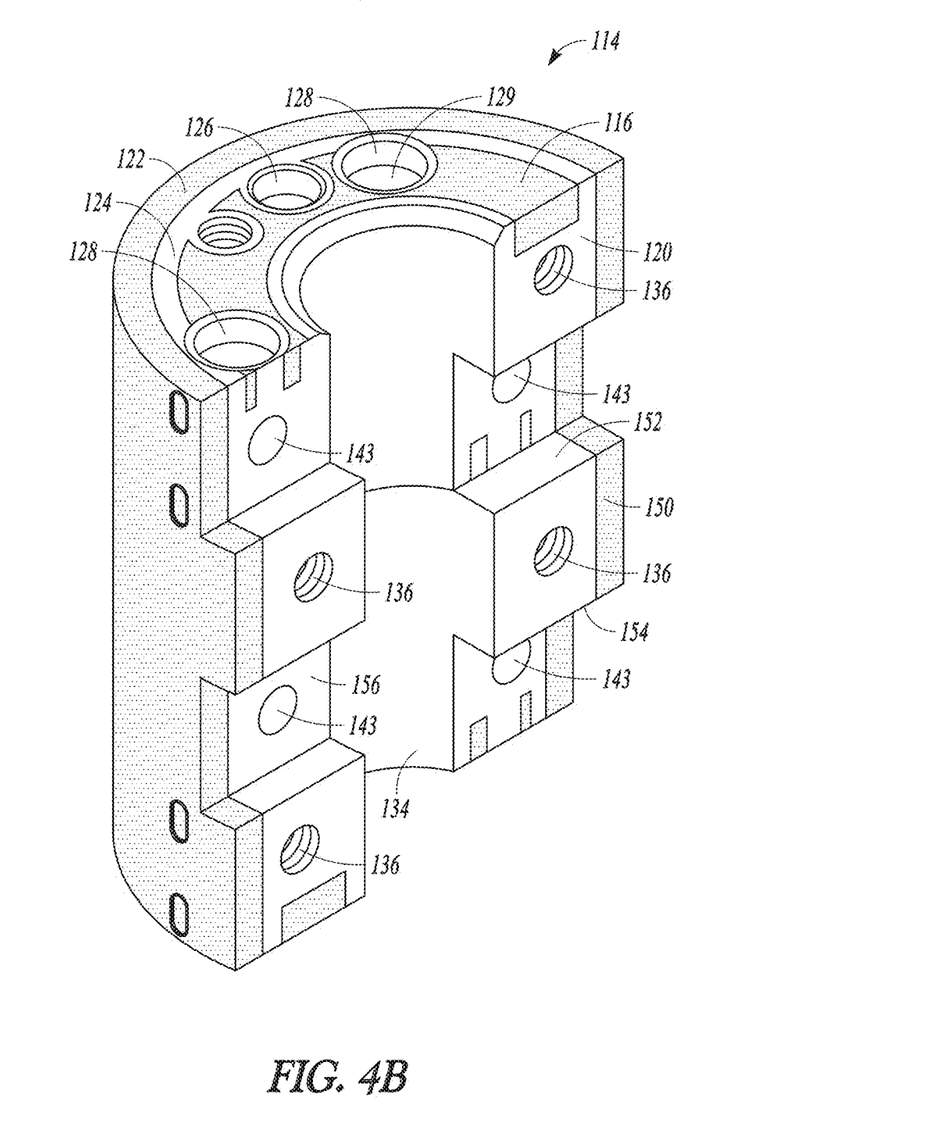
FIG. 4B is a bottom perspective view of the modular implant part of FIG. 4A.
Figure 4C:
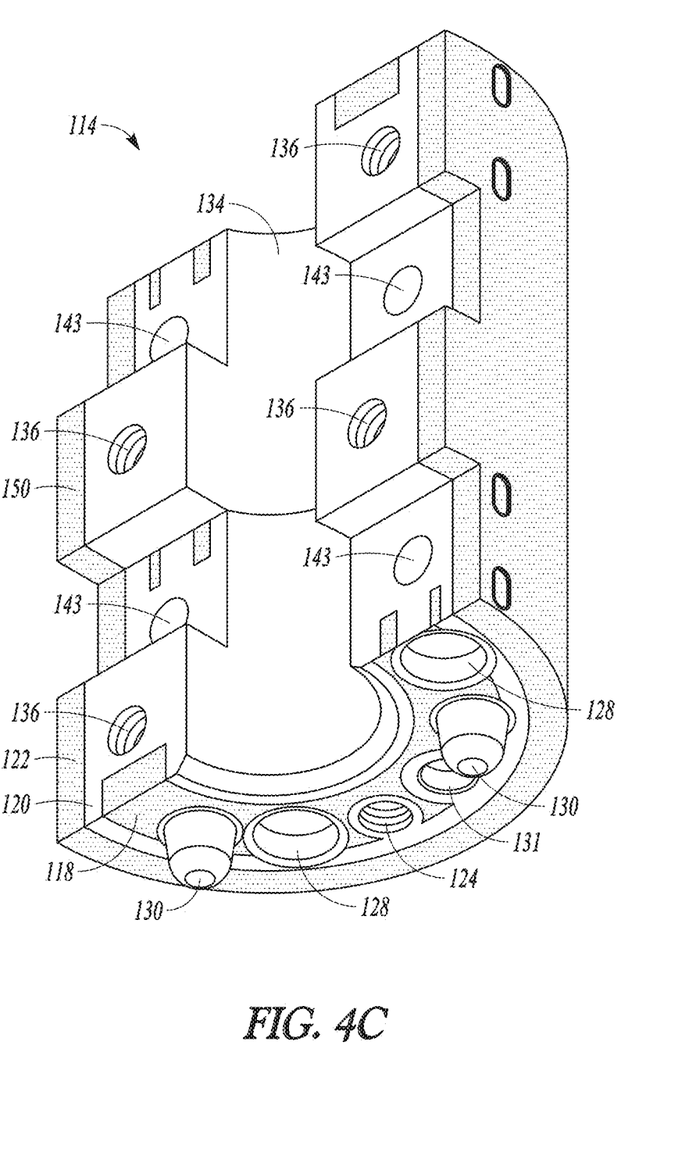
FIG. 4C is a top perspective view.
Figure 4D:
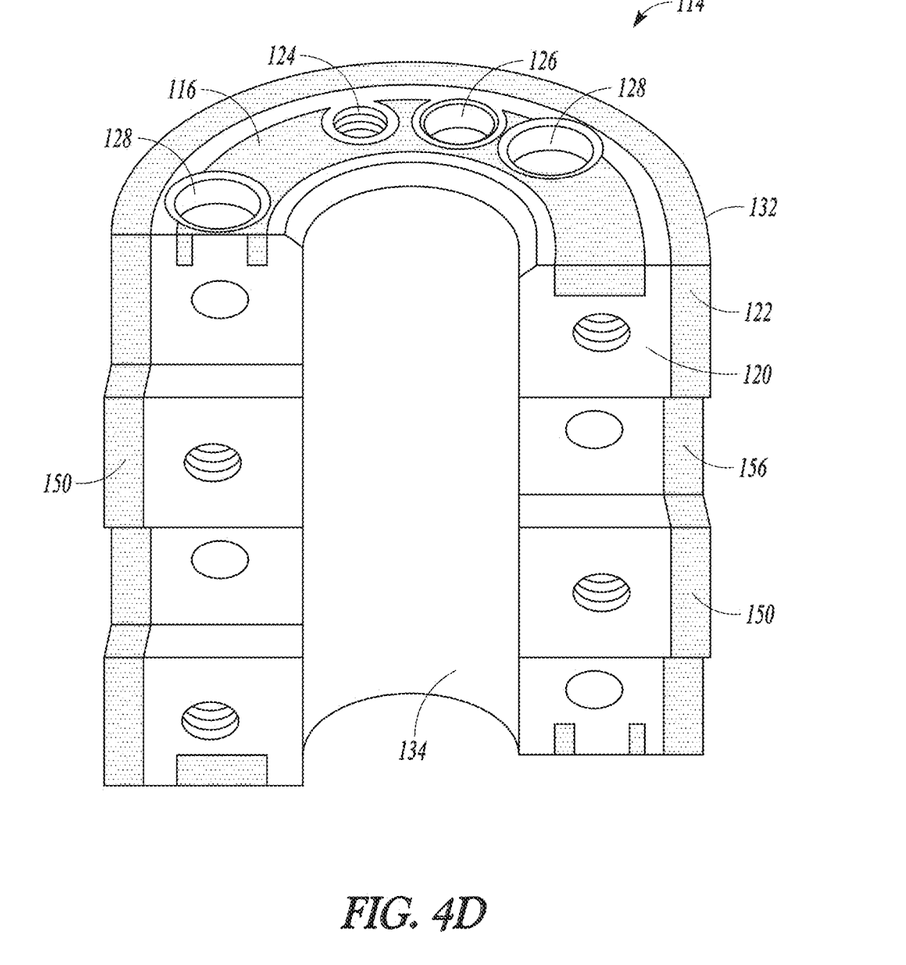
FIG. 4D is an internal side view.

Referring to FIGS. 3A-C, modular implant part 14 can have first 16 and second 18 opposing surfaces. First surface 16 can include a threaded hole 24 capable of interacting with a fixation member 44, such as a screw, post, pin, or other fixation device. Of course, hole 24 can alternatively be designed to receive press-fit fixation members, bayonet fixation members, or other locking devices. Thus, hole 24 could be non-threaded and include a taper or other press-fit structure to interact with a similarly-tapered fixation member. Threaded hole 24 can extend entirely through modular implant part 14 and a portion or substantially all of the internal walls of hole 24 can be threaded.

First surface 16 of modular implant part 14 can also include a counterbored hole 26 recessed within first surface 16. Counterbored hole 26 can have a first section (not shown) that is sized, both vertically and horizontally, to accept a head 45 of a fixation member 44 so that head 45 is flush with or recessed below first surface 16. Counterbored hole 26 can also include a second section (not shown) that is sized, both vertically and horizontally, to accept a shaft 46 of a fixation member 44. The second section (not shown) can open out into second surface 18 of modular implant part 14 so as to define an opening 31 in second surface 18. In an example, a step (not shown) can be formed between the first and second sections of counterbored hole 26 for head 45 to seat on and ensure head 45 cannot travel past the step into the second section of counterbored hole 26. Counterbored hole 26 can extend entirely through modular implant part 14.

Referring to FIG. 3B, first surface 16 can further include counterbored recesses 28. Counterbored recesses 28 can define a floor surface 29 closing recesses 28. Thus, counterbored recesses 28, in an example, can extend only partway into modular implant part 14 and not entirely through part 14. Counterbored recesses 28 can be sized and shaped, as described more fully below, to receive a post or peg of another modular implant part.

Referring to FIG. 3C, modular implant part 14 can also include a second surface 18 with a different arrangement for hole 24 and counterbored recesses 28. Second surface 18 can further include one (1) or more pegs or posts 30, in an example two (2) posts 30, which extend from second surface 18. The arrangement for hole 24, counterbored recesses 28, and posts 30 can be such that, if modular implant part 14 were flipped, its second surface 18 could engage with second surface 18 of another modular implant part 14.

Due to the above arrangement, a first modular implant part 14 can be stacked vertically on a second modular implant part 14. In an example, second surfaces 18 of a pair of first and second modular implant parts 14 can be arranged in opposition to each other and posts 30 can be inserted into counterbored recesses 28. Further, a series of fixation members 44 can be inserted into counterbored holes 26 starting from first surface 16 of each implant part 14 so that head 45 rests within the first section (not shown) of each hole 26 and shaft 46 extends into and through the second section (not shown) of hole 26. Shaft 46 can be threaded and can therefore extend through opening 31 in second surface 18 of each implant part 14 and thread into the threaded holes 24 of the other implant part 14. Thus, head 45 can rest on the step (not shown) of hole 26 and shaft 46 can engage threaded hole 24 of the other modular implant part 14 so that the first and second modular implant parts 14 are engaged and stacked vertically. Further, first surfaces 16 of the first and second implant parts 14 can be arranged to face and engage the patient's bone and define a substantially flat surface, in an example without pegs or posts, to engage the bone.

In an example, a second set of first and second modular implant parts 14 could also be stacked vertically in the manner discussed above. The first and second sets of modular implant parts 14 can then be engaged together horizontally using fixation members 47 to create a modular implant system 8 according to an example of the disclosure. In this example, each of modular implant parts 14 can have a height that is approximately ten millimeters (10 mm), thus giving modular implant system 8 a total height of twenty millimeters (20 mm).

As shown in FIGS. 1 and 3A-C, modular implant part 14 can also include an inner side 34 and an outer side 32. In an example, referring to FIG. 3A, outer side 32 can include a counterbored hole 38 that can be designed similarly to counterbored hole 26. Thus, counterbored hole 38 can include a first section 37 that is sized, vertically and horizontally, to receive a head 48 of a second fixation member 47 so that head 48 is flush with or recessed below outer side 32. Likewise, counterbored hole 38 can include a second section 39 that is sized to receive a shaft 49 of second fixation member 47. A step 41 can be formed between first 37 and second 39 sections and form a seat configured to engage with head 48 of second fixation member 47 (e.g., to ensure that head 48 cannot travel into second section 39). Further, outer side 32 can also include a hole 36 that is threaded along part or all of hole 36.

Referring to FIGS. 3B-C, on inner side 34 of modular implant part 14, second section 39 of counterbored hole 38 can define an opening 43. Likewise, on inner side 34, hole 36 can be present. Hole 36 can be threaded at least from inner side 34 some distance internally towards outer side 32 so that second fixation member 47 can engage the threading. With the above features, it is possible to horizontally engage a set of modular implant parts 14 using fixation members 47.

A pair of modular implant parts 14 can also be engaged horizontally in a non-stacked arrangement using fixation members 47, as shown in FIG. 1. As an example, first and second modular implant parts 14 can be arranged next to each other, as shown in FIG. 1, and fixation members 47 can be inserted into counterbored holes 38 and threaded into holes 36. This can horizontally join together modular implant parts 14 to define a modular bone augment that can then be stacked vertically with another modular bone augment (e.g., of a different height).

Referring to FIG. 1, in an assembled condition modular implant parts 14 can collectively define a cylindrical core comprised of inner sides 34 that is sized and shaped to receive a portion of an intramedullary implant 200, for example a shaft 201 thereof. In an example, intramedullary implant 200 can be a tibial nail.

A further example of a modular implant part 114 is illustrated in FIGS. 4A-D. Modular implant part 114 can be identical to modular implant part 14 described above, except for several discrepancies detailed below. Thus, like reference numerals are used for like elements, except in the 100 series, and only the differences between modular implant parts 14, 114 will be discussed. Although a particular reference numeral may be missing from the drawings related to modular implant part 114, it is to be understood that modular implant part 114 can be identical to modular implant part 14, except for the differences discussed below.

Modular implant part 114 can be identical to modular implant part 14, except that modular implant part 114 can be of a different height and include one (1) or more ledges 150 for engagement of a pair of first and second implant parts 114. Such ledges 150 can have a first surface 152 that extends substantially perpendicular or alternatively at an angle to the respective implant part 114, and a second opposing surface 154 that extends substantially perpendicular or alternatively at an angle to the respective implant part 114. Ledges 150 can alternate along modular implant part 114, such that a recess 156 is defined where ledges 150 are not. Thus, an alternating pattern of ledges 150 and recesses 156 can extend along modular implant part 114 to more or less define a toothed type of arrangement. Ledges 150 and recesses 156 can be arranged to intermesh with each other so that a first modular implant part 114 can be horizontally attached to a second modular implant part 114. In an alternate example, ledges 150 and recesses 156 can be shaped to form a dovetail engagement between a particular ledge 150 and a recess 156.

A pair of first and second modular implant parts 114 can be joined horizontally using fixation members 47 and then stacked with a pair of first and second modular implant parts 14, similar to as shown in FIG. 1. For example, a number of modular implant parts 14, 114 can be joined horizontally using fixation members 47, and then the modular implant parts 14, 114 can be stacked on top of each other vertically, similar to as shown in FIG. 1. Fixation members 44 can be used to join the implant parts 14, 114 together vertically so they remain in their stacked arrangement. It is thus possible to stack two (2) sets of first and second modular implant parts 14, 114 to create a modular implant system usable as a bone augment. Since modular implant parts 14, 114 can be of different heights, the above stacking can provide flexibility to the surgeon to suit the particular patient at hand. In a particular example, modular implant part 114 can have a height of approximately forty millimeters (40 mm) while modular implant part 14 can have a height of approximately ten millimeters (10 mm). Thus, the combined height of modular implant parts 14, 114 when stacked as discussed above can be fifty millimeters (50 mm).

Modular implant parts 14, 114, when engaged together, can also define an inner core comprised of inner sides 34, 134 that has a diameter of about ten millimeters (10 mm), thirteen millimeters (13 mm), or sixteen and a half millimeters (16.5 mm). In an example, the inner core can have a diameter that is sized to receive a portion of an intramedullary implant for the tibia, humerus, or femur, for instance a shaft thereof. Further, an outer diameter of modular implant parts 14, 114, when assembled, can be sized to approximate the diameters of the tibia, humerus, or femur. In an example, the outer diameter can be twenty five millimeters (25 mm), thirty five millimeters (35 mm), or forty two millimeters (42 mm). Modular implant parts 14, 114 can therefore be assembled and stacked in various arrangements to define a modular implant system of various heights. All dimensions are, of course, exemplary and other dimensions are contemplated.

Figure 2:
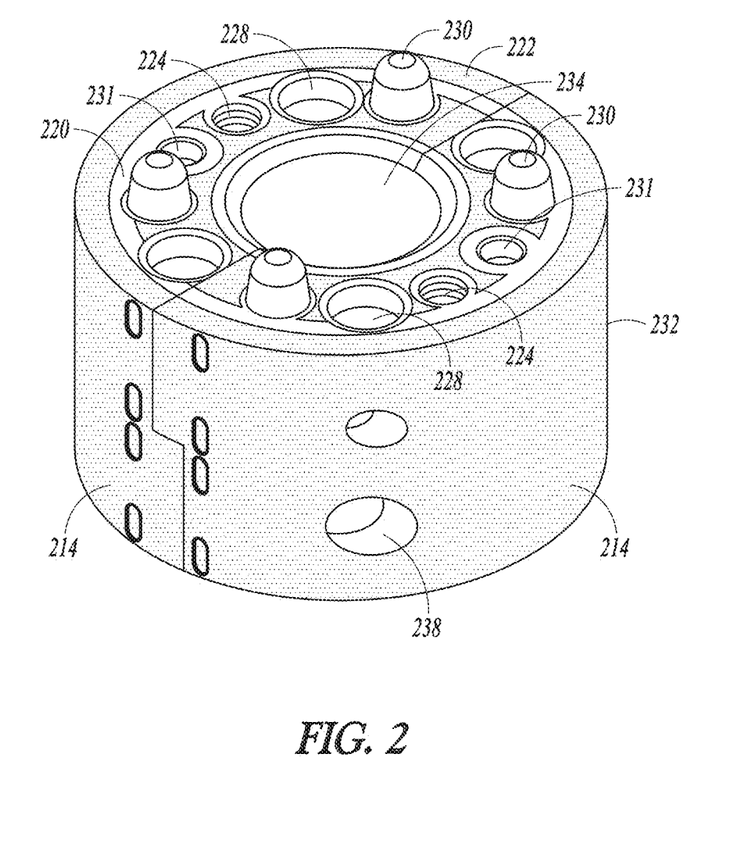
FIG. 2 is an assembled view of part of the modular implant system of FIG. 1.

Another modular implant part 214 is shown in the exploded view of FIG. 1, and in an assembled view in FIG. 2. Modular implant part 214 can be identical to modular implant parts 14, 114, except that a different number of ledges 250 and recesses 256 are used. In addition, modular implant part 214 can be of a different height, in an example approximately twenty millimeters (20 mm). As above, in this example like reference numerals are used for like elements, except in the 200 series, and only the differences between modular implant parts 14, 114, 214 are discussed. Although a particular reference numeral may be missing from the drawings related to modular implant part 214, it is to be understood that modular implant part 214 can be identical to modular implant parts 14, 114, except for the differences outlined.

Figure 6A:
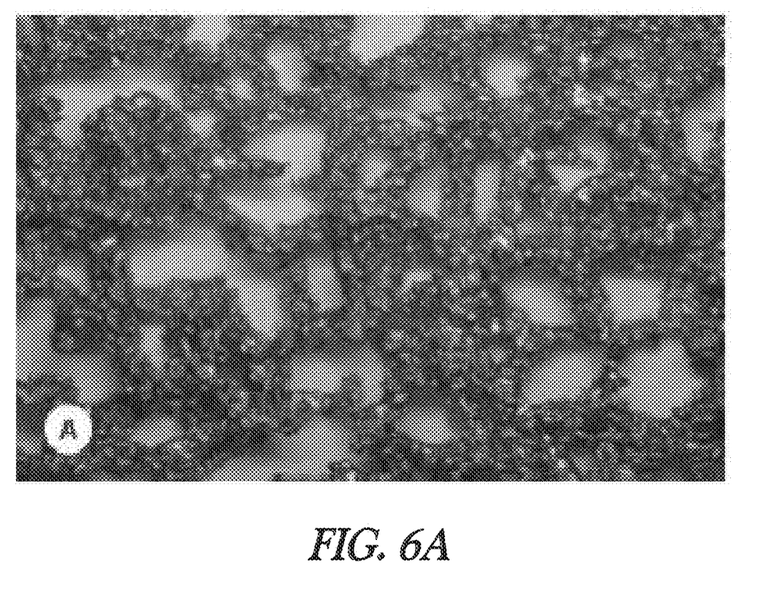
FIGS. 6A-B illustrate OsseoTi® and natural human cancellous bone, respectively.
Figure 6B:
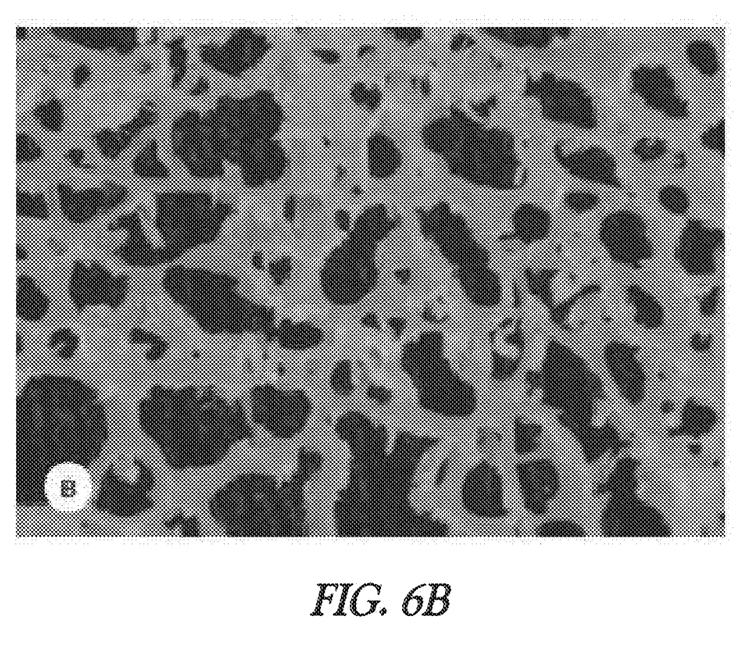

Any of modular implant parts 14, 114, 214 can be manufactured using an additive manufacturing process and/or be composed of different materials to improve the bone-integration features of such implant parts 14, 114, 214. As an example, 3D printing, selective laser melting, selective laser sintering, or any other suitable additive manufacturing process can be used to manufacture implant parts 14, 114, 214. Further, portions of implant parts 14, 114, 214 can be formed of a substantially non-porous biocompatible material (e.g., a non-porous metal or metal alloy), while other portions of implant parts 14, 114, 214 can be formed of a porous biocompatible material to enhance bone ingrowth. In an example, the porous biocompatible material can be OsseoTi®, which is commercially available from Biomet Manufacturing, LLC (Warsaw, Ind., USA). Briefly, OsseoTi® can be a titanium alloy, in an example Ti6Al4V, that is highly biocompatible, has high corrosion resistance, and includes a highly interconnected porous architecture that mimics the porous structure of human cancellous bone. FIGS. 6A-B illustrate the architecture of OsseoTi® (FIG. 6A) as compared to human cancellous bone (FIG. 6B). As shown, the architecture of OsseoTi® mimics that of cancellous bone. OsseoTi® can therefore enhance bone integration and ingrowth. In an exemplary implementation, the OsseoTi® porous metal construct can include a porosity of 70%. In another example, the substantially non-porous biocompatible material can be titanium. In the figures, the porous sections of implant parts 14, 114, 214 are designated by a stipple fill and the non-porous sections are designated by plain white.

As shown in the figures, implant parts 14, 114, 214 can have non-porous sections 20, 120, 220 and porous sections 22, 122, 222 composed of any of the materials discussed above. As noted, porous sections 22, 122, 222 are designated by a stipple fill in the figures, while non-porous sections 20, 120, 220 are designated by plain white in the figures. Porous sections 22, 122, 222 can have an architecture that replicates natural cancellous bone, as with OsseoTi®. Further, in an example, non-porous sections 20, 120, 220 of implant parts 14, 114, 214 can be formed in areas where structural integrity is needed for implant parts 14, 114, 214. For instance, non-porous sections 20, 120, 220 can compose inner sides 34, 134, 234 so that the inner core of the modular augment is structurally sound and able to accept a portion of an intramedullary implant 200. Further, non-porous sections 20, 120, 220 can compose any of holes 24, 124, 224, counterbored holes 26, 126, 226, and/or counterbored recesses 28, 128, 228, in any combination. Likewise, non-porous sections 20, 120, 220 can compose part or all of holes 36, 136, 236 and/or counterbored holes 38, 138, 238. By contrast, porous sections 22, 122, 222 can form outer sides 32, 132, 232 of implant parts 14, 114, 214. Portions or substantially all of first surface 16, 116, 216 and/or second surface 18, 118, 218 can also comprise porous sections 22, 122, 222.

Referring to FIGS. 1, 3B-C and 4B-C, in an example non-porous sections 20, 120, 220 can define a modified I-beam shaped structure that forms a core of implant parts 14, 114, 214, and porous sections 22, 122, 222 can occupy outer surface portions of the modified I-beam so that porous sections 22, 122, 222 can interface with bone and promote bone ingrowth. The structure is referred to herein as a modified I-beam since parts of holes 24, 124, 224, counterbored holes 26, 126, 226, and/or counterbored recesses 28, 128, 228 can be formed of non-porous material as described above, which can interrupt the traditional I-beam shape.

To provide additional initial mechanical strength and stability to the porous structure, the porous structure may be infiltrated with filler material such as a non-resorbable polymer or a resorbable polymer. Examples of non-resorbable polymers for infiltration of the porous structure can include a polyaryl ether ketone (PAEK), such as polyether ketone ketone (PEKK), polyether ether ketone (PEEK), polyether ketone ether ketone ketone (PEKEKK), polymethylacrylate (PMMA), polyetherimide, polysulfone, and polyphenolsulfone. Examples of resorbable polymers may include Polylactide (PLA), Polyglycolic acid (PGA), polylactic co-glycolic acid (PLGA), polyhydroxybutyrate (PHB), polyhydroxyvalerate (PHV), Poly-L-lactide (PLLA), and copolymers thereof, polycaprolactone, polyanhydrides, and polyorthoesters.

The pores of the porous parts disclosed herein may also be filled with other materials, such as bone growth proteins, antibiotics, or human derived, animal derived, or synthetic bone grafting materials. Each of the materials or combinations of any of these materials may provide a clinical advantage to the porous portion.

Various different modular implant systems, such as modular implant system 8 shown in FIG. 1, can be created using modular implant parts 14, 114, 214. In an example, a set of modular implant parts 14 can be stacked with a set of modular implant parts 114 and fixed together via fixation members 44, 47 to create a modular implant system that has a height of fifty millimeters (50 mm). In another example, a set of modular implant parts 14 can be stacked with a set of modular implant parts 214 and fixed together via fixation members 44, 47 to create a modular implant system that has a height of thirty millimeters (30 mm). Thus, modular implant systems of various heights can be formed using modular implant parts 14, 114, 214 to replace and/or augment different lengths of bone according to patient needs. In an example, a horizontally-joined pair of modular implant parts 14, a horizontally-joined pair of modular implant parts 114, or a horizontally-joined pair of modular implant parts 214 can be stacked vertically in any combination to create a modular implant system with an appropriate height. As noted previously, modular implant part 14 can have a height often millimeters (10 mm), modular implant part 114 can have a height of forty millimeters (40 mm), and modular implant part 214 can have a height of twenty millimeters (20 mm). Thus, many different height variations are possible.

Referring to FIG. 1, for example, a pair of modular implant parts 14 can be stacked with a pair of modular implant parts 214 and fixed together with fixation members 44, 47. When fixed together, first surfaces 16, 216 of implant parts 14, 214 can be exposed to a patient's bone. Thus, a bone-contacting surface can be presented by part of first surfaces 16, 216 that is relatively flat and does not include posts or pegs extending therefrom. In addition, porous sections 22, 222 can occupy parts of first surfaces 16, 216 and can define outer sides 32, 232 so that bone ingrowth can occur into such porous sections 22, 222 once in contact with bone. In addition, as recognized above, it is contemplated that porous sections 22, 222 can be used along with other bone ingrowth material, such as bone grafts, resorbable polymers, bone growth proteins, etc. to further facilitate bone ingrowth.

Figure 5:
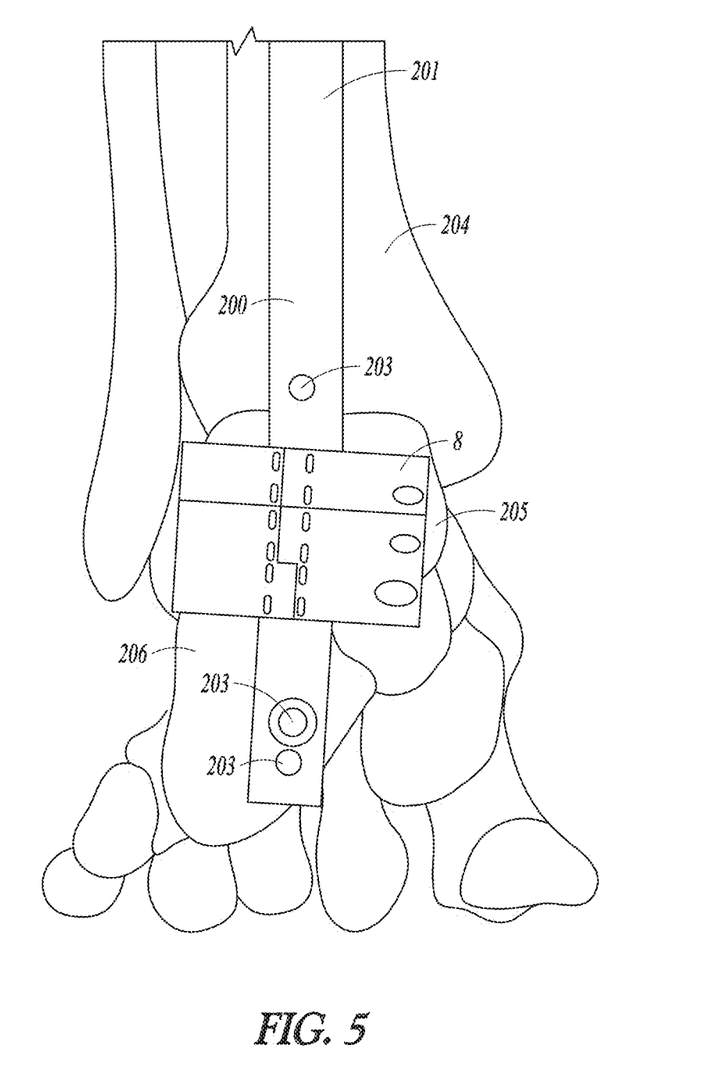
FIG. 5 is a back view of an intramedullary implant and a modular implant system implanted in a patient's ankle.

FIG. 5 illustrates an exemplary use of a modular implant system 8 in an ankle fusion procedure. As shown in FIG. 5, a patient's ankle can be defined by, amongst other bones, the tibia 204, talus 205, and calcaneus 206. In some cases, such as in a failed ankle replacement, portions of tibia 204 and/or talus 205, or even all of talus 205, can become diseased or degraded. The modular implant systems disclosed herein can operate to partially or entirely replace a diseased talus 205, replace only diseased or degraded portions of talus 205 and tibia 204, or replace talus 205 entirely in addition to diseased or degraded portions of tibia 204. Such modular implant systems can also be used with an intramedullary implant 200, as detailed below. Although the below procedure is an ankle fusion, it is to be understood that any of the modular implant systems discussed herein can be used with intramedullary implants in other areas of the body in a like manner (e.g., femoral intramedullary implants, humeral intramedullary implants, etc.)

First, a surgeon can make an incision on a first side of the patient's ankle and expose skin and tissue of the patient so that the ankle can be visualized. Subsequently, intramedullary implant 200 can be inserted through a plantar aspect of the patient's calcaneus 206, through talus 205, and into the intramedullary canal of tibia 204, as shown in FIG. 5. Prior to or after inserting intramedullary implant 200, diseased portions of talus 205 and/or tibia 204 can be removed to make room for a modular implant system. With implant 200 inserted into bone, a modular implant system can be assembled around implant 200 according to the length of bone that was removed from talus 205 and/or tibia 204. For instance, if a thirty millimeter (30 mm) void is needed to be filled by virtue of the fact that the surgeon removed about that length of bone from talus 205 and/or tibia 204, a modular implant system can be assembled that has a height of thirty millimeters (30 mm).

As an example, initially a first set of implant parts 14, 214 can be stacked together vertically and fixed to each other using a plurality of fixation members 44. This can create a half-moon structure composed of the first set of implant parts 14, 214. For instance, second surface 18, 218 of implant parts 14, 214 can be arranged to face each other and posts 30, 230 can be inserted into engagement with counterbored recesses 28, 228. Further, several fixation members 44 can be inserted through counterbored holes 26, 226 on first surface 16, 216 of implant parts 14, 214 and into threaded holes 24, 224 to fix implant parts 14, 214 together in a stacked relationship. With implant parts 14, 214 stacked together, a thirty millimeter (30 mm) half-moon structure can be created, which can be inserted onto implant 200 extending through the patient's ankle. For instance, inner sides 34, 234 defined by implant parts 14, 114 can be slid over shaft 201 of implant 200 so that the part conforms to shaft 201. The first set of implant parts 14, 214 in their vertical stacked arrangement can then be rotated about shaft 201 so that a corresponding set of second implant parts 14, 214, in a stacked arrangement, can be horizontally attached to the first set of implant parts 14, 214. For instance, a second set of implant parts 14, 214 can be vertically stacked and fixed together using fixation members 44 in the same manner as discussed above to create a second thirty millimeter (30 mm) half-moon structure. The second thirty millimeter (30 mm) half-moon structure composed of the second set of implant parts 14, 214 can then be horizontally attached to the first set of implant parts 14, 214, which in an example can already be inserted onto shaft 201 of implant 200. Collectively, the first and second sets of implant parts 14, 214, when horizontally attached together, define a modular implant system that replaces the void previously created by the surgeon in removing diseased parts of talus 205 and/or tibia 204. For instance, a full-moon structure composed of the first and second sets of implant parts 14, 214 can be created by horizontally joining the half-moon structures.

The first and second sets of implant parts 14, 214 can be fixed together horizontally using fixation members 47. For example, fixation members 47 can be inserted through counterbored holes 38, 238 and into threaded holes 36, 236 of implant parts 14, 214 on a first side of the full-moon structure. Then, the modular implant system can be rotated about shaft 201 of implant 200 to allow fixation members 47 to be inserted through counterbored holes 38, 238 and into threaded holes 36, 236 at a second side of the full-moon structure. Subsequently, the adjoining bones in the ankle can be released and allowed to contact first surfaces 16, 216 of implant parts 14, 214 to substantially lock the modular implant system rotationally and allow bone ingrowth into the modular implant system.

Suitable distraction instrumentation for tibia 204 and/or talus 205 can be used to allow rotation of the modular implant system as discussed above relative to shaft 201 of implant 200. For instance, the surgeon can use suitable distraction instrumentation to keep tibia 204 and talus 205 (if present) separated by a distance that is large enough so that first surfaces 16, 216 of implant parts 14, 214 do not contact tibia 204 and/or talus 205 during implantation. Then, when implant parts 14, 214 are assembled over shaft 201 of implant 200, the distraction instrumentation can be removed and tibia 204 and talus 205 (if present) can return to their original states and become seated on first surfaces 16, 216. The modular implant system can then become rotationally stable due to contact with surrounding bone, and can fill the void previously created by the surgeon to provide for improved bone ingrowth and facilitate the ankle fusion process. In the final condition, shaft 201 of implant 200 can extend through the inner cores comprised of inner sides 34, 234 of implant parts 14, 214, as shown in FIG. 5. Additionally, suitable fixation members can be inserted through openings 203 in intramedullary implant 200 to further compress tibia 204 and/or talus 205 against the modular implant system and fix the bones of the ankle in place for proper fusion.

Of course, different modular implant systems are contemplated by the present disclosure, as discussed above, and can be created to fill a fifty millimeter (50 mm) void in bone, a forty millimeter (40 mm) void in bone, or an eighty millimeter (80 mm) void in bone, merely as examples. The modular implant systems described herein can therefore be used in instances where amputation might be a consideration because of, for instance, a failed ankle replacement resulting in significant amounts of diseased or degraded bone. Another example where large amounts of diseased bone might be present, and thus the modular implant systems disclosed herein would be usable, is with cancer.

Alternate variations of bone augments are also envisioned. For example, a one-piece horseshoe version is contemplated in which a core of the augment is a non-porous biocompatible material (e.g., any of the non-porous materials discussed previously) that is covered entirely or substantially entirely by a layer of porous material (e.g., any of the porous materials discussed above). The augment can have a "horseshoe" shape where the core defines a tube portion that conforms to the shape of shaft 201 of implant 200. Thus, the core can define a partially-cylindrical tube that can be inserted over shaft 201 of implant 200. In an example, the partially-cylindrical tube can extend over one-hundred and eighty degrees (180°), but be somewhat flexible so that the tube can flex and snap over shaft 201 of implant 200. In another example, the shape of the tube can be patient-matched or anatomic in cross-section as opposed to being cylindrical.

In another alternate variation, any of inner sides 34, 134, 234 can be coated with a polymer or incorporate a polymer sleeve that can interact with shaft 201 of implant 200. In this way, the polymer coating or sleeve can interface with shaft 201 and reduce scratching or other damage to shaft 201. In a further example, any of the inner cores comprised of inner sides 34, 134, 234 can be shaped to key with a particular-shaped shaft 201 of implant 200. For instance, any of the inner cores comprised of inner sides 34, 134, 234 can be polygon-shaped, oval, or obround and engage with a like-shaped shaft 201 of implant 200 to establish a non-rotational engagement between the inner core and implant 200.

In a further variation of the surgical method, it is contemplated that a surgeon can pre-assemble any of implant parts 14, 114, 214 in a stacked arrangement as discussed above to create a modular implant system, implant the modular implant system, and then insert implant 200 through the patient's ankle and into the inner core comprised of inner sides 34, 134, 234 (as applicable depending upon which implant parts are used for the modular implant system). In this variation or the other examples herein, the ends of inner sides 34, 134, 234 can include a chamfer to ease insertion of implant 200 into the modular implant system.

In still a further variation, any of outer sides 32, 132, 232 can include grooves designed to assist interfacing with bone graft material and improve bone ingrowth for the finally-constructed modular implant system.

It will be readily understood to those skilled in the art that various other changes in the details, material, and arrangements of the parts and method stages which have been described and illustrated in order to explain the nature of the inventive subject matter can be made without departing from the principles and scope of the inventive subject matter as expressed in the subjoined claims. For example, the order of method steps or stages can be altered from that described above, as would be appreciated by a person of skill in the art.

It will also be appreciated that the various dependent claims, examples, and the features set forth therein can be combined in different ways than presented above and/or in the initial claims. For instance, any feature(s) from the above examples can be shared with others of the described examples, and/or a feature(s) from a particular dependent claim may be shared with another dependent or independent claim, in combinations that would be understood by a person of skill in the art.

What is claimed is:

1. A modular implant system comprising:
    a first modular implant part having first and second opposing surfaces and an inner core section;
    a second modular implant part having first and second opposing surfaces and an inner core section, wherein the first and second modular implant parts are engageable and, when engaged, the inner core sections of the first and second modular implant parts collectively define an inner core of the modular implant system that has a shape that corresponds to a shape of a portion of an intramedullary implant;
    a third modular implant part having first and second opposing surfaces and an inner core section; and
    a fourth modular implant part having first and second opposing surfaces and an inner core section, wherein the third and fourth modular implant parts are engageable and, when engaged, the inner core sections of the third and fourth modular implant parts collectively define an inner core of the modular implant system that has a shape that corresponds to the shape of the portion of the intramedullary implant, and wherein the second surfaces of the third and fourth modular implant parts are engageable with the second surfaces of the first and second modular implant parts, such that the third and fourth implant parts are arrangeable on the first and second modular implant parts in a stacked configuration;

wherein the second surface of the first modular implant part includes a post and the second surface of the third modular implant part includes a recess sized and shaped to receive the post.

2. The modular implant system of claim 1, wherein the first and second implant parts have a first height and the third and fourth implant parts have a second height that is different than the first height.

3. The modular implant system of rein the shape of the inner core of the modular implant system is round.

4. The modular implant system of claim 1, wherein the first surface of any of the first and second modular implant parts is at least partially composed of a porous biocompatible material that has an architecture that replicates natural cancellous bone.

5. The modular implant system of claim 4, wherein the first surface of any of the first and second modular implant parts is at least partially composed of a substantially non-porous biocompatible material.

6. The modular implant system of claim 1, wherein the inner core of the modular implant system is composed of a substantially non-porous biocompatible material.

7. The modular implant system of claim 1, wherein the first modular implant part includes a first locking hole and the second modular implant part includes a first hole, and wherein when the first and second modular implant parts are engaged, the first locking hole and the first hole are aligned.

8. The modular implant system of claim 7, further comprising a fixation member insertable through the first hole and into the first locking hole, the fixation member being configured to engage the first locking hole and lockingly join the first modular implant part to the second modular implant part.

9. A modular implant system comprising:
a first modular implant part having first and second opposing surfaces and an inner core section;
a second modular implant part having first and first opposing surfaces and an inner core section, wherein the first and second modular implant parts are engageable and, when engaged, the inner core sections of the first and second modular implant parts collectively define an inner core of the modular implant system that has a shape that corresponds to a shape of a portion of an intramedullary implant;
a third modular implant part having first and second opposing surfaces and an inner core section;
a fourth modular implant part having first and second opposing surfaces and an inner core section, wherein the third and fourth modular implant parts are engageable and, when engaged, the inner core sections of the third and fourth modular implant parts collectively define an inner core of the modular implant system that has a shape that corresponds to the shape of the portion of the intramedullary implant, and wherein the second surfaces of the third and fourth modular implant parts are engageable with the second surfaces of the first and second modular implant parts, such that the third and fourth implant parts are arrangeable on the first and second modular implant parts in a stacked configuration;
wherein the first modular implant part includes a first hole and the third modular implant part includes a first locking hole, and wherein when the first modular implant part is stacked on the third modular implant part, the first hole and the first locking hole of the third modular implant part are aligned;
a fixation member insertable through the second hole and into the first locking hole of the third modular implant part, the fixation member being configured to engage the first locking hole of the third modular implant part and lockingly join the first modular implant part to the third modular implant part.

10. The modular implant system of claim 7, wherein the first locking hole of the first modular implant part and the first hole of the second modular implant part are threaded.

11. The modular implant system of claim 9, wherein the first and second implant parts have a first height and the third and fourth implant parts have a second height that is different than the first height.

12. The modular implant system of claim 9, wherein the second surface of the first modular implant part includes a post and the first surface of the third modular implant part includes a recess sized and shaped to receive the post.

13. The modular implant system of claim 9, wherein the shape of the inner core of the modular implant system is round.

14. The modular implant system of claim 9, wherein the first surface of any of the first and second modular implant parts is at least partially composed of a porous biocompatible material that has an architecture that replicates natural cancellous bone.

15. The modular implant system of claim 14, wherein the first surface of any of the first and second modular implant parts is at least partially composed of a substantially non-porous biocompatible material.

16. The modular implant system of claim 9, wherein the inner core of the modular implant system is composed of a substantially non-porous biocompatible material.

17. The modular implant system of claim 9, wherein the first modular implant part includes a first locking hole and the second modular implant part includes a first hole, and wherein when the first and second modular implant parts are engaged, the first locking hole and the first hole are aligned.

18. The modular implant system of claim 17, further comprising a second fixation member insertable through the first hole of the second modular implant part and into the first locking hole of the first modular implant part, the second fixation member being configured to engage the first locking hole and lockingly join the first modular implant part to the second modular implant part.

19. The modular implant system of claim 17, wherein the first locking hole of the first modular implant part and the first hole of the second modular implant part are threaded.

20. The modular implant system of claim 1, wherein the first modular implant part includes a second hole and the third modular implant part includes a first locking hole, and wherein when the first modular implant part is stacked on the third modular implant part, the second hole and the first locking hole of the third modular implant part are aligned and further comprising a fixation member insertable through the second hole and into the first locking hole of the third modular implant part, the fixation member being configured to engage the first locking hole of the third modular implant part and lockingly join the first modular implant part to the third modular implant part.

* * * * *

UNITED STATES PATENT AND TRADEMARK OFFICE
CERTIFICATE OF CORRECTION

PATENT NO. : 10,716,603 B2  
APPLICATION NO. : 15/901221  
DATED : July 21, 2020  
INVENTOR(S) : Van Dyke et al.

Page 1 of 1

It is certified that error appears in the above-identified patent and that said Letters Patent is hereby corrected as shown below:

In the Claims

Column 13, Line 12, Claim 3, delete "rein" and insert --claim 1, wherein-- therefor Column 13, Line 40, Claim 9, delete "first" and insert --second-- therefor Column 14, Line 4, Claim 9, delete "second" and insert --first-- therefor Signed and Sealed this  
Twenty-second Day of September, 2020

Andrei Iancu  
*Director of the United States Patent and Trademark Office*